United States Patent [19]

Uchiyama et al.

[11] Patent Number: 4,673,693

[45] Date of Patent: Jun. 16, 1987

[54] PROCESS FOR PREPARING OXYGEN-CONTAINING ORGANIC COMPOUNDS

[75] Inventors: Soichi Uchiyama; Toshiaki Hayasaka; Yasuo Ohbayashi, all of Sodegaura, Japan

[73] Assignee: Research Association for Petroleum Alternatives Development, Tokyo, Japan

[21] Appl. No.: 790,416

[22] Filed: Oct. 23, 1985

[30] Foreign Application Priority Data

Nov. 5, 1984 [JP] Japan ................................ 59-231295

[51] Int. Cl.$^4$ ............................................ C07C 27/06
[52] U.S. Cl. ...................................... 518/713; 502/329
[58] Field of Search .......................................... 518/713

[56] References Cited

U.S. PATENT DOCUMENTS 4,564,643 1/1986 Shibata et al. .
4,582,858 4/1986 Shibata et al. .

FOREIGN PATENT DOCUMENTS 110357 6/1984 European Pat. Off. ............ 518/713

Primary Examiner—Howard T. Mars
Attorney, Agent, or Firm—Frishauf, Holtz, Goodman & Woodward

[57] ABSTRACT

A process for preparing oxygen-containing organic compounds from synthesis gas which comprises contacting the synthesis gas with a solid catalyst prepared by the steps of: mixing (A) a copper compound, (B) a nickel compound and (C) a zinc compound; calcining the mixture; mixing the calcined product with (D) a potassium compound; and then reducing the resulting mixture.

The selectivity of alcohols such as ethanol and propanol is high in the process of the present invention. The catalyst of the present invention can be used effectively over long periods of time, since the dissipation of the nickel component in the catalyst during the reaction is decreased.

5 Claims, No Drawings

PROCESS FOR PREPARING OXYGEN-CONTAINING ORGANIC COMPOUNDS

BACKGROUND OF THE INVENTION

The present invention relates to a process for preparing oxygen-containing organic compounds. More particularly, it is concerned with a process for preparing oxygen-containing organic compounds such as alcohols, particularly those having at least two carbon atoms from synthesis gas consisting of carbon monoxide and hydrogen with high selectivity by the use of a specific catalyst.

Various methods have been proposed to produce oxygen-containing organic compounds such as alcohols from a synthesis gas as a starting material. For example, a method using a catalyst comprising Cu/Co/Cr, Fe, V or Mn/rare earth element/ alkali metal or alkaline earth metal (Japanese Patent Application Laid-Open No. 85530/80), and a method using an alloy catalyst comprising Cu/Ti/Cr, Mo, Mn, Rh, Co, Pt or Fe/ alkali metal or alkaline earth metal (Japanese Patent Application Laid-Open No. 122045/83) are known. The former method, however, has a disadvantage in that the activity of the catalyst is not sufficiently high. This is because in preparation of the catalyst, the alkali metal or alkaline earth metal is added by the solution dipping process and, therefore, the whole catalyst becomes alkaline, leading to a reduction in the activity thereof. Also the latter method has disadvantages in that much time and labor is needed in preparation of the catalyst because it is an alloy catalyst and, as oxygen-containing organic compounds formed, methanol and ethanol are mainly produced.

As a result of extensive investigations to overcome the above problems and to develop a process for efficiently preparing alcohols by the use of a catalyst which can be easily prepared, a method has been proposed using a solid substance catalyst which is prepared by the steps of calcining a mixture of (A) a copper compound, (B) a nickel compound, and (C) a compound containing at least one metal selected from the metals belonging to Groups II, III and IV of the Periodic Table and the metals belonging to the fourth period of Groups V, VI and VII, impregnating the calcined product with (D) an alkali metal compound and/or alkaline earth metal compound, calcining the impregnated product, and then reducing it (see Japanese Patent Application Laid-Open No. 98024/84 and U.S. Pat. No. 4,582,858). It has been revealed, however, that the above method permits efficient preparation of the desired oxygen-containing organic compounds and is satisfactory for practical use, but that it has a disadvantage in that nickel is dissipated during its long term use, resulting in a decrease of the catalyst activity.

Under such circumstances, further investigations have been made, and it has now been found that if nickel is used in combination with a specific component, the dissipation of nickel can be decreased and the proportion of alcohols, particularly those having at least two carbon atoms in the formed oxygen-containing compound is increased.

SUMMARY OF THE INVENTION

An object of the present invention is to provide a process for preparing oxygen-containing organic compounds, particularly alcohols having at least two carbon atoms with high efficiency from synthesis gas.

Another object of the present invention is to provide a process for preparing oxygen-containing organic compounds from synthesis gas by the use of a catalyst which can be easily prepared and can be used over long periods of time, i.e., has a long service life Still another object of the present invention is to provide a process for preparing alcohols having at least two carbon atoms, such as ethanol and propanol, from synthesis gas with high selectivity.

It has now been found that the objects can be attained by using a catalyst which is prepared by the steps of mixing (A) a copper compound, (B) a nickel compound and (C) a zinc compound, calcining the mixture, mixing the product thus obtained with (D) a potassium compound, and then reducing the resulting mixture.

Accordingly the present invention relates to a process for preparing oxygen-containing organic compounds from synthesis gas which comprises contacting the synthesis gas with a solid catalyst prepared by the steps of mixing (A) a copper compound, (B) a nickel compound and (C) a zinc compound, calcining the mixture, mixing the calcined product with (D) a potassium compound, and then reducing the resulting mixture.

DETAILED DESCRIPTION OF THE INVENTION

In preparation of the catalyst for use in the process of the present invention, (A) a copper compound, (B) a nickel compound, and (C) a zinc compound are first mixed and calcined. The copper compound (A) is not critical in type; any copper compounds can be used as long as they contain copper. Usually water-soluble copper compounds such as copper nitrate, copper sulfate, and copper chloride are preferably used. In connection with the nickel compound (B), any nickel compounds can be used as long as they contain nickel. For example, water-soluble nickel compounds such as nickel nitrate, nickel sulfate, and nickel chloride are preferably used. As the zinc compound (C), various types of compounds containing zinc can be used. In particular, water-soluble zinc compounds such as zinc nitrate, zinc sulfate, and zinc chloride are preferably used.

In mixing the compounds (A), (B) and (C), they are mixed in the form of an aqueous solution or aqueous suspension and then precipitated by adjusting the pH through addition of a coprecipitation agent, such as sodium carbonate, sodium hydroxide, or potassium hydroxide, at room temperature or while heating. Then the precipitate is aged, if necessary, and washed with water, dried and then calcined at a temperature of 200° to 500° C.

The above-calcined product is mixed with (D) a potassium compound and then reduced to prepare the catalyst of the present invention. In this case, it is preferred for the potassium compound to be added in a dried powder form. Alternatively the potassium compound may be applied in the form of an aqueous solution so as to impregnate the calcined product therewith. Typical examples of the potassium compound are potassium carbonate, potassium acetate, and potassium hydroxide. In a case that (D) the calcined product is impregnated with an aqueous solution of the potassium compound, it is preferred that the resulting mass be further calcined. This calcination temperature is preferably chosen within the range of 100° to 400° C.

The composition of the above-obtained catalyst precursor varies with the amounts of the compounds (A), (B), (C) and (D) used. Preferably the mole ratio of the compounds (A), (B), (C) and (D) (calculated as oxides) is as follows:

(A): 0.05 to 0.5
(B): 0.01 to 0.55
(C): 0.1 to 0.7
(D): 0.005 to 0.16

The reduction of the above mixture is carried out using a reducing agent such as hydrogen or carbon monoxide at a temperature of 200° to 400° C. The solid substance thus obtained can be effectively used as a catalyst for the process of the present invention. When the compounds (A), (B), (C) and (D) are mixed at the same time and calcined, the potassium compound (D) tends to be dispersed only unevenly and to be localized, so that a satisfactory catalyst cannot be obtained.

In accordance with the present invention, synthesis gas, i.e., a mixture of hydrogen and carbon monoxide is contacted with the above-prepared solid substance as a catalyst to prepare oxygen-containing organic compounds. The composition of the synthesis gas used as a feedstock is not critical. In general, synthesis gas in which the molar ratio of hydrogen to carbon monoxide (hydrogen/carbon monoxide) is 1:3 to 3:1 is suitably used.

Other conditions in the practice of the present invention can be determined appropriately. The reaction temperature is 200° to 500° C. and preferably 240° to 400° C. The reaction pressure may be relatively low. In general, the reaction pressure is 20 to 200 kg/cm$^2$G (kilograms per square centimeter by gauge) and preferably 40 to 100 kg/cm$^2$G. The gas hourly space velocity (GHSV) is 500 to 100,000 hr$^{-1}$ (per hour) and preferably 1,000 to 50,000 hr$^{-1}$.

The present invention yields various advantages by using a catalyst having the above-specified components. Some of the major advantages are shown below.

The dissipation of the nickel component during the reaction is decreased and thus the catalyst of the present invention can be used effectively over long periods of time. Alcohols, particularly those having at least two carbon atoms, such as ethanol and propanol can be prepared with high selectivity and efficiency. Since the reaction pressure is sufficient when relatively low, production costs including equipment and running costs can be greatly decreased. Since the proportion of methanol and higher alcohols in the oxygen-containing organic compound is high, the organic compound is suitable as an alcohol to be blended with gasoline for cars or as a starting material for preparation of various chemical products.

Accordingly the process of the present invention is of high industrial value.

The present invention is described in greater detail with reference to the following examples.

EXAMPLE 1

An aqueous solution (Aqueous Solution I) (1.5 liters) containing 29.0 grams of copper nitrate (trihydrate), 17.4 grams of nickel nitrate (hexahydrate), and 35.7 grams of zinc nitrate (hexahydrate) was heated to 60° C. Independently, 1.5 liters of an aqueous solution (Aqueous Solution II) containing 40.6 grams of sodium carbonate (anhydrous) was heated to 60° C.

The above two solutions I, II were mixed rapidly so as to completely achieve precipitation. The resulting mixture was filtered and the precipitate was fully washed with water. The precipitate was dried at 120° C. for about 10 hours and then calcined at 450° C. for 2 hours. After calcination, 2.33 grams of powdered potassium carbonate (anhydrous) was added to the above-calcined product, and the resulting mixture was ground. Then graphite was added to the ground product in an amount of 2 wt % (percents by weight) based on the weight of the ground product. The resulting mixture was pelletized by the use of a pellet-molding machine and then ground to obtain 16-32 mesh particles. In the catalyst precursor thus obtained Cu:Ni:Zn:K = 2:1:2:0.64 (molar ratio).

This catalyst precursor (1 milliliter) was packed in a stainless steel reaction tube (SUS) and while passing a mixed gas of hydrogen and nitrogen ($H_2/N_2 = 1/9$ (molar ratio)) as a reducing gas through the tube at GHSV of 4,000 hr$^{-1}$, the catalyst precursor was gradually heated and reduced at 240° C. for 20 hours to prepare a catalyst.

Synthesis gas consisting carbon monoxide and hydrogen (carbon monoxide/hydrogen = ½ by mole) was passed through the reaction tube at GHSV of 4,000 hr$^{-1}$. The pressure of the synthesis gas was gradually increased to 60 kg/cm$^2$G, and when the pressure reached 60 kg/cm$^2$G, the synthesis gas was heated to a predetermined temperature as shown in Table 1.

Reaction products were introduced into a gas chromatography column through a tube maintained at 200° C. without causing condensation at an outlet of the reaction tube, and analyzed. As fillers for the column, active carbon, Porapak-Q (produced by Water Corp.), and Porapak-R (produced by Water Corp.) were used.

After the reaction was stopped, the amount of nickel remaining in the catalyst of the reaction tube was measured and compared with the amount of nickel in the fresh catalyst prior to the reaction. This measurement was carried out by the atomic absorption method.

The results are shown in Table 1.

COMPARATIVE EXAMPLE 1

A catalyst precursor was prepared in the same manner as in Example 1 except that 1.5 liters of an aqueous solution containing 24.2 grams of copper nitrate (trihydrate), 17.4 grams of nickel nitrate (hexahydrate), and 40.0 grams of chromium nitrate was used as Aqueous Solution I, and 1.5 liters of an aqueous solution containing 45.4 grams of sodium carbonate (anhydrous) was used as Aqueous Solution II. The composition of the catalyst precursor thus obtained was Cu:Ni:Cr:K = 2:1:2:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 2

A catalyst precursor was prepared in the same manner as in Example 1 except that 1.5 liters of an aqueous solution containing 24.2 grams of copper nitrate (trihydrate), 17.4 grams of nickel nitrate (hexahydrate), and 37.5 grams of aluminum nitrate (nonahydrate) was used as Aqueous Solution I, and 1.5 liters of an aqueous solution containing 45.1 grams of sodium carbonate (anhydrous) was used as Aqueous Solution II. The composition of the catalyst precursor thus obtained was Cu:Ni:Al:K=2:1:1.6:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 3

A catalyst precursor was prepared in the same manner as in Example 1 except that 1.5 liters of an aqueous solution containing 24.2 grams of copper nitrate (trihydrate), 17.4 grams of nickel nitrate (hexahydrate), and 120 g of titanium sulfate (30% aqueous solution) was used as Aqueous Solution I, and 1.5 liters of an aqueous solution containing 64.0 grams of sodium carbonate (anhydrous) was used as Aqueous Solution II. The composition of the catalyst precursor thus obtained was Cu:Ni:Ti:K=2:1:2:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 4

A catalyst precursor was prepared in the same manner as in Example 1 except that 1.5 liters of an aqueous solution containing 24.2 grams of copper nitrate (trihydrate), 17.4 grams of nickel nitrate (hexahydrate), and 12.8 grams of magnesium nitrate (hexahydrate) was used as Aqueous Solution I, and 1.5 liters of an aqueous solution containing 25.2 grams of sodium carbonate (anhydrous) was used as Aqueous Solution II. The composition of the catalyst precursor thus obtained was Cu:Ni:Mg:K=2:1:1:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 5

A catalyst precursor was prepared in the same manner as in Example 1 except that 2.04 grams of powdered sodium carbonate (anhydrous) was added to the calcined product in place of potassium carbonate. The composition of the catalyst precursor was Cu:Ni:Zn:Na=2:1:2:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 6

A catalyst precursor was prepared in the same manner as in Example 1 except that 6.23 grams of powdered cesium carbonate was added to the calcined product in place of potassium carbonate. The composition of the catalyst precursor was Cu:Ni:Zn:Cs=2:1:2:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 7

A catalyst precursor was prepared in the same manner as in Example 1 except that 3.84 grams of powdered calcium carbonate was added to the calcined product in place of potassium carbonate. The composition of the catalyst precursor was Cu:Ni:Zn:Ca=2:1:2:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 8

A catalyst precursor was prepared in the same manner as in Example 1 except that 7.58 grams of powdered barium carbonate was added to the calcined product in place of potassium carbonate. The composition of the catalyst precursor was Cu:Ni:Zn:Ba=2:1:2:0.64 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

COMPARATIVE EXAMPLE 9

A catalyst precursor was prepared in the same manner as in Example 1 except that the alkali metal or alkaline earth metal compound was not added to the calcined product. The composition of the catalyst precursor was Cu:Ni:Zn=2:1:2 (molar ratio).

Subsequently, in the same manner as in Example 1, the catalyst precursor was treated to prepare a catalyst and the synthesis gas was converted with the catalyst. Reaction products and the amount of nickel in the used catalyst were measured also in the same manner as in Example 1.

The results are shown in Table 1.

TABLE 1

| Run No. | Reaction Temperature (°C.) | Conversion of Carbon Monoxide*[1] (%) | Selectivity of Oxygen-Containing Organic Compounds*[2] (%) | Proportion of Oxygen-Containing Organic Compounds having Two or More Carbon Atoms*[3] (%) |
| --- | --- | --- | --- | --- |
| Example 1 | 338 | 18 | 65 | 57 |
| Comparative | 290 | 21 | 66 | 14 |

TABLE 1-continued

| Example 1 | | | | |
|---|---|---|---|---|
| Comparative Example 2 | 270 | 5 | 64 | 16 |
| Comparative Example 3 | 331 | 18 | 24 | 26 |
| Comparative Example 4 | 291 | 5 | 60 | 20 |
| Comparative Example 5 | 346 | 15 | 64 | 14 |
| Comparative Example 6 | 371 | 12 | 59 | 34 |
| Comparative Example 7 | 344 | 13 | 65 | 2 |
| Comparative Example 8 | 333 | 12 | 69 | 5 |
| Comparative Example 9 | 309 | 20 | 70 | 9 |

| | Composition of Formed Oxygen-Containing Organic Compounds (wt %) | | | | | Amount of Nickel dissipated[*4] |
|---|---|---|---|---|---|---|
| Run No. | Methanol | Ethanol | $C_3$ Alcohols | $C_4$ Alcohols | Others | (wt %) |
| Example 1 | 43 | 32 | 18 | 2 | 5 | 0 |
| Comparative Example 1 | 86 | 9 | 1 | 2 | 2 | 35 |
| Comparative Example 2 | 84 | 7 | 3 | 5 | 1 | 11 |
| Comparative Example 3 | 74 | 14 | 3 | 6 | 3 | 4 |
| Comparative Example 4 | 80 | 9 | 2 | <1 | 8 | 15 |
| Comparative Example 5 | 86 | 10 | 4 | 0 | 0 | 0 |
| Comparative Example 6 | 66 | 15 | 14 | 3 | 2 | 0 |
| Comparative Example 7 | 98 | 2 | 0 | 0 | 0 | 0 |
| Comparative Example 8 | 91 | 3 | 1 | 1 | 4 | 0 |
| Comparative Example 9 | 91 | 4 | 1 | <1 | 4 | 0 |

Note:

[*1] Conversion of carbon monoxide = $\frac{\text{(Conversion carbon monoxide (mole))} - \text{(Formed carbon dioxide (mole))}}{\text{Introduced carbon monoxide (mole)}} \times 100$

[*2] Selectivity of oxygen-containing organic compound = $\frac{\text{(Carbon monoxide converted into oxygen-containing organic compound (mole))}}{\text{(Converted carbon monoxide (mole))} - \text{(Formed carbon dioxide (mole))}} \times 100$

[*3] Proportion of oxygen-containing organic compounds having two or more carbon atoms = $\frac{\text{Weight of formed oxygen-containing organic compounds having two or more carbon atoms}}{\text{Weight of formed oxygen-containing organic compounds}} \times 100$

[*4] Amount of nickel dissipated (determined after 50 hours) =

$$\left(1 - \frac{\text{Amount of nickel in the used catalyst (based on the weight of copper)}}{\text{Amount of nickel in the fresh catalyst (based on the weight of copper)}} \times 100 \right)$$

What is claimed is:

1. A process for preparing alcohols from hydrogen and carbon monoxide and increasing the selectivity of alcohol having at least two carbon atoms which comprises contacting the hydrogen and carbon monoxide with a solid catalyst prepared by the steps of: mixing (A) a copper compound, (B) a nickel compound and (C) a zinc compound; calcining the mixture to obtain a calcined product; mixing (D) a potassium compound with the calcined product; and then reducing the resulting mixture, wherein the mole ratio of the compounds (A), (B), (C) and (D), calculated as oxides, is
   (A) 0.05 to 0.5,
   (B) 0.01 to 0.55,
   (C) 0.1 to 0.7, and
   (D) 0.005 to 0.16, and recovering the mixture of alcohols thusly produced.

2. The process of claim 1 wherein said mole ratio of hydrogen to carbon monoxide is from 1:3 to 3:1; and wherein said hydrogen and carbon monoxide are contacted with said catalyst at a temperature of from 200° to 500° C., a pressure of from 20 to 200 kg/cm²G and an hourly space velocity of from 500 to 100,000 hr$^{-1}$.

3. The process of claim 1 wherein said mole ratio of hydrogen to carbon monoxide is from 1:3 to 3:1, and wherein said hydrogen and carbon monoxide are contacted with said catalyst at a temperature of from 240° to 400° C., a pressure of from 40 to 100 kg/cm²G and an hourly space velocity of from 1,000 to 50,000 hr$^{-1}$.

4. The process of claim 3 wherein said catalyst was prepared by reducing said resulting mixture with hydrogen or carbon monoxide at a temperature of from 200° to 400° C.

5. The process of claim 4 wherein the catalyst mixture which was reduced has a molar ratio of copper: nickel: zinc: potassium of 2:1:2:0.64.

* * * * *

UNITED STATES PATENT AND TRADEMARK OFFICE
CERTIFICATE OF CORRECTION

PATENT NO. : 4,673,693
DATED : June 16, 1987
INVENTOR(S) : UCHIYAMA et al

It is certified that error appears in the above-identified patent and that said Letters Patent is hereby corrected as shown below:

Column 7, line 49 (Claim 1):

Change "alcohol" to --alcohols--.

Signed and Sealed this

Fifteenth Day of December, 1998

Attest:

DOUGLAS B. COMER

*Attesting Officer*       Acting Commissioner of Patents and Trademarks